United States Patent [19]

Alagy et al.

[11] 4,145,560

[45] Mar. 20, 1979

[54] PROCESS FOR MANUFACTURING TEREPHTHALIC ACID BY OXIDATION OF PARAXYLENE

[75] Inventors: Jacques Alagy, Lyon; Quang Dang Vu, Paris, both of France

[73] Assignee: Institut Francais du Petrole, Rueil-Malmaison, France

[21] Appl. No.: 676,818

[22] Filed: Apr. 14, 1976

[30] Foreign Application Priority Data

Apr. 14, 1975 [FR] France .................................. 75 11749

[51] Int. Cl.$^2$ ............................................. C07C 51/33
[52] U.S. Cl. .................................................. 562/412
[58] Field of Search ..................... 260/524 R; 562/412

[56] References Cited

U.S. PATENT DOCUMENTS 3,170,768  2/1965  Baldwin ........................... 260/524 R

*Primary Examiner*—A. Siegel
*Attorney, Agent, or Firm*—Millen & White

[57] ABSTRACT

Process for manufacturing a benzene carboxylic acid by oxidation of an alkyl substituted benzene, and in particular for manufacturing terephthalic acid by oxidation of paraxylene, in which said benzene carboxylic acid, in solution in an aliphatic monocarboxylic acid, such as acetic acid, is oxidized by means of a gas containing molecular oxygen at a temperature T from 80° to 260° C. under a pressure from 2 to 30 kg/cm$^2$, in the presence of a transition metal compound, in at least one reactor whose internal wall is maintained during the whole reaction time at a temperature, in °C., from T − 10 to T + 100.

10 Claims, No Drawings

PROCESS FOR MANUFACTURING TEREPHTHALIC ACID BY OXIDATION OF PARAXYLENE

This invention concerns a process for manufacturing benzene carboxylic acids by oxidation of benzenes substituted by alkyl groups. There can be used as starting materials ortho, meta or paraxylene, cymenes, methylethylbenzenes, diisopropylbenzenes, ethylbutylbenzenes, toluene etc. The process of the invention is particularly convenient for the oxidation of xylenes to benzene-dicarboxylic acids; the invention relates more particularly to an improved process for manufacturing terephthalic acid by oxidation of paraxylene.

It has been proposed to oxidize paraxylene in solution in an aliphatic monocarboxylic acid such, for example, as acetic acid or homologues thereof, at a temperature generally from 80° to 260° C., in the presence of a heavy metal catalyst, by means of molecular oxygen in at least one reaction zone.

Paraxylene is first converted to paratoluic acid which, if the oxidation is continued, is itself converted to terephthalic acid. Processes of this type have been described for example in the U.S. Pat. No. 2,245,528 and in the French Pat. Nos. 1,504,431 and 1,504,432.

The yields of terephthalic acid and the reaction velocities are reasonably high. However, in a field where competition is severe, each improvement, even of low extent, may convert a satisfactory process to an economical, industrially profitable process.

In the prior processes of paraxylene oxidation to terephthalic acid in the liquid phase, a gas containing molecular oxygen (generally air) is passed through a solution of a mixture of paraxylene with a monocarboxylic acid, in the presence of a catalyst.

Terephthalic acid, thus produced, appears in the form of a solid dispersed in the reaction mixture. It is separated from the effluent of the reaction zone by filtration, centrifugation or any other convenient means.

Oxygen, which may be used in admixture with an inert gas, for example as air, is introduced into the reaction zone either at ordinary temperature, or preferably at a temperature close to that prevailing in the reaction zone; for example the oxygen-containing gas is preheated at a temperature about 10° C. below the reaction temperature or at a higher temperature as described in the Japanese patent application No. 63085/74, or even at a temperature higher than in the reaction zone, for example, 2° to 50° C. and preferably about 5° to 30° C. above the temperature in the reaction zone. By this procedure, it is possible to avoid cooling, in the vicinity of the injection duct, of the gas containing molecular oxygen and accordingly, to avoid any clogging in the vicinity of the duct for gas injection. However, this does not prevent a slight cooling at this level. Of course, this cooling is of small extent, but, after a long period, it results in clogging of said duct, which clogging results in the formation of terephthalic acid crystals, which may require the periodical interruption of the process for cleaning the apparatus.

Moreover, in the conventional or improved apparatus, with or without preheating of the oxygen-containing gas, deposits of resins and various solids appear at different points of the internal wall of the reactor, which progressively extend to the whole internal wall of the reactor. These solids adhering to of the walls will necessarily cause a discontinuance of the operation e.g. about each month, in order to to clean the reactor cleaning. Moreover, in addition to fouling the reactor walls, the formed resins, consisting essentially of terephthalic acid having a long residence time in the reactor, result in the formation of more or less substantial amounts of by-products (particularly 4-carboxy benzaldehyde) which are undesirable in the reactor effluent, since these by-products progressively inhibit the reaction, decrease the total yield and spoil the produced terephthalic acid as well as the catalyst.

All the above-mentioned disadvantages disappear when proceeding according to this invention where, T being the reaction temperature, (° C.) the internal wall of the reaction zone must be heated before the reaction and maintained by any convenient means and during the whole reaction time, at a temperature ranging from T $-10$ to T$+100$, expressed in ° C., preferably from T $-5$ to T $+ 80$, and particularly from T $-4$ to T $+ 80$, more specifically, from T $-2$ to T $+ 60$.

The term "by any convenient means" covers any system for maintaining the reactor walls at the desired temperature. It is possible, for example, to use a reactor whose walls are provided with a double jacket through which circulates any liquid or fluid whose physical and/or chemical properties are not altered at the operating conditions to which it is subjected.

It is also possible to heat the walls of the reactor by electric heating means or a coil embedded in a heat transmitting cement or any other means which seems convenient to those skilled in the art.

This procedure, according to the invention, results in a substantial decrease of by-products and various deposits and, accordingly, in the maintenance over long periods of a high yield of terephthalic acid.

The conditions for conducting the reaction of xylene oxidation are known and need not to be further described in detail.

It is reminded that there can be used, as oxidation catalyst, a compound of a transition metal, preferably a salt of cobalt or manganese (e.g. cobalt acetate, cobalt propionate, a cobalt oleate, a manganese naphthenate, cobalt bromide or manganese bromide) or a mixture of several of these compounds.

The oxidation catalyst may be used, for example, in an amount of from 0.01 to 50 (and preferably from 0.01 to 5) parts per part by weight of paraxylene.

Conventional initiators may also be used, for example olefins, ethers, ketones, aldehydes, peroxides or similar compounds or a source of bromine ions (e.g. hydrobromic acid) or bromine.

The solvent for paraxylene is a monocarboxylic acid, containing for example from 2 to 8 carbon atoms, and preferably acetic acid. There is used for example, from 1 to 20 and preferably from 2 to 10 parts by weight of carboxylic acid per part by weight of paraxylene.

The general conditions of the reaction correspond to a temperature in the range, for example, from about 80° to 260° C., and generally, super-atmospheric pressures from about 2 to 35 kg/cm$^2$.

According to another aspect of the invention, in addition to controlling the inner wall temperature, the gas containing molecular oxygen, before introduction to the reaction zone, is preheated to a temperature not lower than 10° C. below the reaction temperature.

The process is particularly adapted to be performed continuously for the production of benzene dicarboxylic acids.

The following examples illustrate the invention.

EXAMPLE 1

In a reactor operated in a continuous manner, we introduce 4.5 kg/h of paraxylene, 50 kg/h of acetic acid, 0.31 kg/h of hydrobromic acid, 0.51 kg/h of cobalt acetate tetrahydrate and 20 m³/h of air (volume measured at 0° C. under 760 mm Hg). The temperature is 210° C. and the pressure 25 atmospheres at the top of the reactor. Air is injected at 200° C.

Several experiments are conducted over a period of 1000 hours. Each experiment is performed in a reactor whose walls are maintained at various temperature; we use a reactor whose walls are formed of a double jacket inside which is circulated a liquid (paraxylene) heated to a suitable temperature for obtaining the desired temperature of the reactor walls. In the following table, the molar yield of terephthalic acid is given after 1000 hours of operation in relation with the average temperature of the reactor walls. When the reactor walls are at a temperature of 150° C. or even 190° C., deposits on these walls are observed after 300 hours. On the contrary, when the temperature of these walls is higher than about 200° C., particularly higher than 205° C., substantially no deposit is observed even after 1000 hours, and after interruption of the operation, it was observed that the apparatus was clean.

| Average Temperature Of The Reactor Walls °C | Molar Yield Of Terephthalic Acid (%) |
|---|---|
| 150 | 87 |
| 190 | 89 |
| 200 | 90,5 |
| 205 | 91 |
| 208 | 92 |
| 210 | 92 |
| 220 | 92 |
| 230 | 92 |

EXAMPLE 2

There is used a titanium autoclave of a 10 liter capacity, equipped with a reflux condenser, a stirrer, an inlet duct for the reactants, a duct for withdrawing the reaction effluent and an inlet duct for an oxygen-containing gas; the reactor is also provided with a jacket with oil circulation for maintaining the walls of the autoclave at a determined temperature. The reaction is conducted at 210° C. under a pressure of 25 kg/cm². The reactor is fed with 3 kg of acetic acid, 4.19 g of cobalt acetate tetrahydrate, 8.83 g of manganese acetate tetrahydrate, 3.83 g of sodium bromide and 480 g of water. We then introduce into the reactor 500 g/h of paraxylene and 1500 g/h of acetic acid having dissolved therein cobalt acetate, manganese acetate and sodium bromide, in the above-mentioned proportions, before starting the reaction (the water content being 5% by weight). We introduce air into the reactor in such an amount that the oxygen content of the effluent gas withdrawn from the reactor is 4% by volume. The reaction is continued for 15 hours while withdrawing the excess of reaction mixture every 30 minutes.

When adjusting the temperature of the oil at the outlet from the reactor jacket to 213° C., it is observed that, at the end of the reaction, no deposit of terephthalic acid occurs on the internal walls of the reactor.

On the contrary, when the temperature of the oil at the outlet from the reactor is adjusted to only 198° C., it is observed, at the end of the reaction, the deposit of a layer of crystals on the internal wall of the reactor; the thickness of this layer is about 4 to 5 mm.

We claim:

1. In a process for manufacturing benzene carboxylic acids by oxidation of benzene substituted with alkyl groups, in at least one reaction zone, in the liquid phase, by means of a gas containing molecular oxygen, in an aliphatic monocarboxylic acid at an average temperature T from about 80° to 260° C., at a pressure from about 2 to 30 kg/cm², in the presence of a transition metal compound as an oxidation catalyst, the improvement in which the internal wall of the reaction zone is preheated and maintained during the whole reaction time at an average temperature, expressed in ° C., from T − 10 to T + 100.

2. A process according to claim 1, in which the wall of the reaction zone is preheated and maintained at an average temperature (° C.) from T − 5 to T + 80.

3. A process according to claim 1, in which the wall of the reaction zone is preheated and maintained at an average temperature (° C.) from T − 2 to T + 60.

4. A process according to claim 1 in which, before introduction into the reaction zone, the gas containing molecular oxygen is preheated to a temperature not lower than 10° C. below the reaction temperature.

5. A process according to claim 1, for manufacturing benzene dicarboxylic acids.

6. A process according to claim 1, for manufacturing terephthalic acid by oxidation of paraxylene.

7. A process according to claim 6, wherein the process is performed in a continuous manner.

8. A process according to claim 2 for manufacturing terephthalic acid by oxidation of paraxylene.

9. A process according to claim 3 for manufacturing terephthalic acid by oxidation of paraxylene.

10. A process according to claim 9 in which, before introduction into the reaction zone, the gas containing molecular oxygen is preheated to a temperature not lower than 10° C. below the reaction temperature.

* * * * *